(12) United States Patent
Lockhart et al.

(10) Patent No.: US 7,270,127 B2
(45) Date of Patent: Sep. 18, 2007

(54) MEDICAMENT RESPIRATORY DELIVERY DEVICE

(75) Inventors: Artis R. Lockhart, Durham, NC (US); Vincent J. Sullivan, Cary, NC (US); Lawrence A. Monahan, Willow Spring, NC (US); Anjana Bhuta Wills, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1127 days.

(21) Appl. No.: 10/233,863

(22) Filed: Sep. 3, 2002

(65) Prior Publication Data

US 2003/0047184 A1 Mar. 13, 2003

Related U.S. Application Data

(63) Continuation of application No. 09/879,714, filed on Jun. 12, 2001, now Pat. No. 6,443,152, which is a continuation-in-part of application No. 09/758,776, filed on Jan. 12, 2001, now Pat. No. 6,722,364.

(51) Int. Cl.
*A61M 15/00* (2006.01)

(52) U.S. Cl. .......................... 128/203.15; 128/203.12; 128/203.21

(58) Field of Classification Search ........... 128/200.14, 128/200.23, 203.12, 203.15, 203.21, 203.23
See application file for complete search history.

(56) References Cited

U.S. PATENT DOCUMENTS

| 2,307,986 | A |   | 1/1943 | Bolte et al. |
| 3,625,213 | A |   | 12/1971 | Brown |
| 3,807,400 | A |   | 4/1974 | Cocozza |
| 3,874,380 | A | * | 4/1975 | Baum .................... 128/200.14 |
| 3,934,585 | A | * | 1/1976 | Maurice ..................... 604/298 |
| 3,949,751 | A | * | 4/1976 | Birch et al. ............ 128/203.15 |
| 4,344,573 | A |   | 8/1982 | De Felice |
| 4,723,691 | A |   | 2/1988 | Minkevitch et al. |
| 4,900,315 | A |   | 2/1990 | Lundqvist et al. |
| 4,962,868 | A |   | 10/1990 | Borchard |
| 5,215,221 | A | * | 6/1993 | Dirksing ...................... 222/94 |
| 5,239,991 | A |   | 8/1993 | Chawla et al. |
| 5,307,953 | A |   | 5/1994 | Regan |
| 5,328,464 | A | * | 7/1994 | Kriesel et al. ................. 604/83 |
| 5,331,954 | A | * | 7/1994 | Rex et al. ............. 128/200.22 |

(Continued)

FOREIGN PATENT DOCUMENTS

GB 1338254 11/1973

(Continued)

OTHER PUBLICATIONS

WO 02/056950 A3 PCT Search Report.

*Primary Examiner*—(Jackie) Tan-Uyen Ho
*Assistant Examiner*—Darwin P. Erezo
(74) *Attorney, Agent, or Firm*—Robert E. West

(57) ABSTRACT

A medicament respiratory delivery device including a housing formed of opposed thermoformed polymeric sheets bonded together having formed therebetween a chamber having a medicament cartridge encapsulated between the sheets, an inlet aligned with a passage through the cartridge having a pierceable closure and an outlet aligned with the passage outlet having a burstable membrane. The device includes a pressure actuator formed as a blister between the sheets and a piercing element having a bow-shaped actuator portion and a shaft which pierces the pierceable closure upon actuation of the pressure actuator, delivering fluid under pressure to the cartridge passage, rupturing the membrane and expressing the medicament.

18 Claims, 3 Drawing Sheets

U.S. PATENT DOCUMENTS

| | | | |
|---|---|---|---|
| 5,349,947 A | 9/1994 | Newhouse et al. | |
| 5,458,135 A * | 10/1995 | Patton et al. | 128/200.14 |
| 5,513,630 A | 5/1996 | Century | |
| 5,533,505 A | 7/1996 | Kallstrand et al. | |
| 5,542,412 A | 8/1996 | Century | |
| 5,547,131 A * | 8/1996 | Brace | 239/309 |
| 5,571,246 A | 11/1996 | Alldredge | |
| 5,601,077 A | 2/1997 | Imbert | |
| 5,619,984 A * | 4/1997 | Hodson et al. | 128/203.15 |
| 5,637,087 A * | 6/1997 | O'Neil et al. | 604/82 |
| 5,702,362 A | 12/1997 | Herold et al. | |
| 5,740,794 A | 4/1998 | Smith et al. | |
| 5,787,881 A | 8/1998 | Chawla | |
| 5,797,392 A | 8/1998 | Keldmann et al. | |
| 5,819,730 A | 10/1998 | Stone et al. | |
| 5,881,716 A * | 3/1999 | Wirch et al. | 128/200.16 |
| 5,881,719 A * | 3/1999 | Gottenauer et al. | 128/203.15 |
| 5,881,720 A | 3/1999 | Vindogradov et al. | |
| 5,894,967 A | 4/1999 | Stahley et al. | |
| 5,918,594 A * | 7/1999 | Asking et al. | 128/203.15 |
| 5,921,236 A * | 7/1999 | Ohki et al. | 128/203.15 |
| 5,941,867 A * | 8/1999 | Kao | 604/416 |
| 5,983,893 A * | 11/1999 | Wetterlin | 128/203.15 |
| 6,065,472 A * | 5/2000 | Anderson et al. | 128/203.21 |
| 6,070,575 A * | 6/2000 | Gonda et al. | 128/203.12 |
| 6,098,619 A * | 8/2000 | Britto et al. | 128/203.15 |
| 6,105,574 A * | 8/2000 | Jahnsson | 128/203.15 |
| 6,209,538 B1 * | 4/2001 | Casper et al. | 128/203.15 |
| 6,214,255 B1 * | 4/2001 | Hekal | 252/194 |
| 6,267,753 B1 * | 7/2001 | Kao | 604/416 |
| 6,286,507 B1 * | 9/2001 | Jahnsson | 128/203.15 |
| 6,308,704 B1 * | 10/2001 | Wennerberg | 128/203.15 |
| 6,443,152 B1 * | 9/2002 | Lockhart et al. | 128/203.21 |
| 6,585,959 B2 * | 7/2003 | Walz et al. | 424/46 |
| 6,606,992 B1 * | 8/2003 | Schuler | 128/203.15 |
| 6,644,309 B2 * | 11/2003 | Casper et al. | 128/203.21 |
| 6,722,364 B2 * | 4/2004 | Connelly et al. | 128/203.15 |
| 6,782,887 B2 * | 8/2004 | Sullivan | 128/203.15 |
| 6,929,005 B2 * | 8/2005 | Sullivan et al. | 128/203.21 |
| 7,040,316 B2 * | 5/2006 | Connelly et al. | 128/203.15 |
| 7,051,734 B2 * | 5/2006 | Casper et al. | 128/203.21 |
| 2002/0092523 A1 * | 7/2002 | Connelly et al. | 128/203.15 |
| 2004/0163645 A1 * | 8/2004 | Connelly et al. | 128/203.15 |
| 2005/0000514 A1 * | 1/2005 | Sullivan et al. | 128/200.24 |
| 2006/0150969 A1 * | 7/2006 | Connelly et al. | 128/200.14 |

FOREIGN PATENT DOCUMENTS

| | | |
|---|---|---|
| GB | 1488719 | 10/1977 |
| WO | WO92/05824 | 4/1992 |
| WO | WO92/06727 | 4/1992 |
| WO | WO97/06842 | 2/1997 |
| WO | WO97/10017 | 3/1997 |
| WO | WO97/25087 | 7/1997 |
| WO | WO97/40876 | 11/1997 |
| WO | WO99/47099 | 9/1999 |
| WO | WO99/56807 | 11/1999 |

* cited by examiner

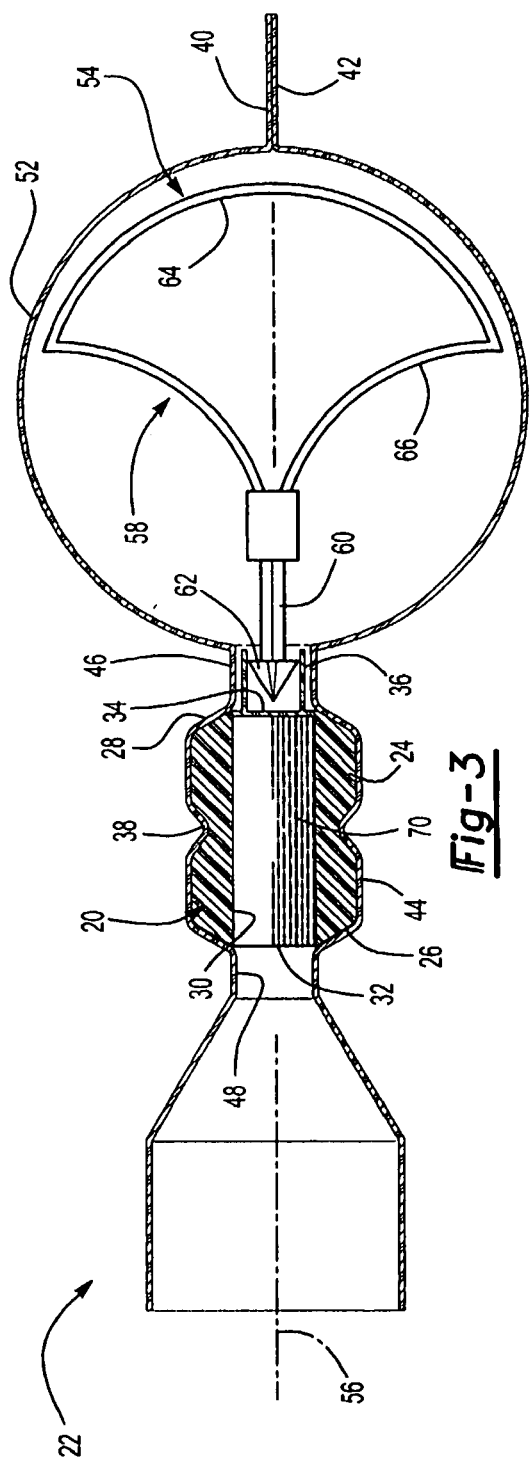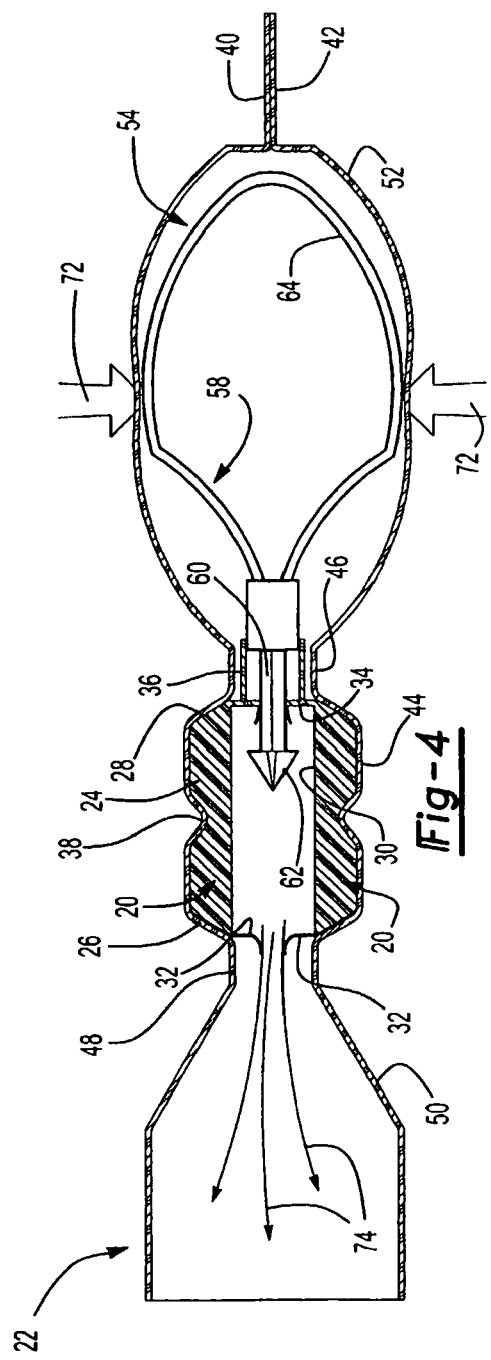

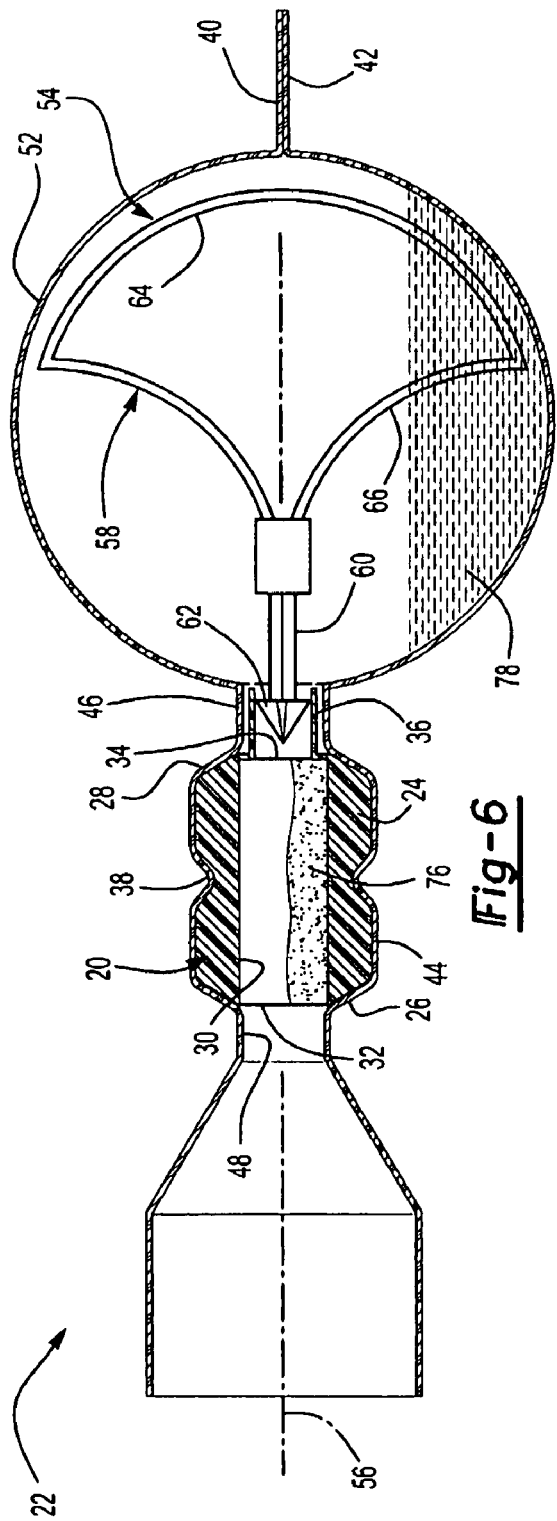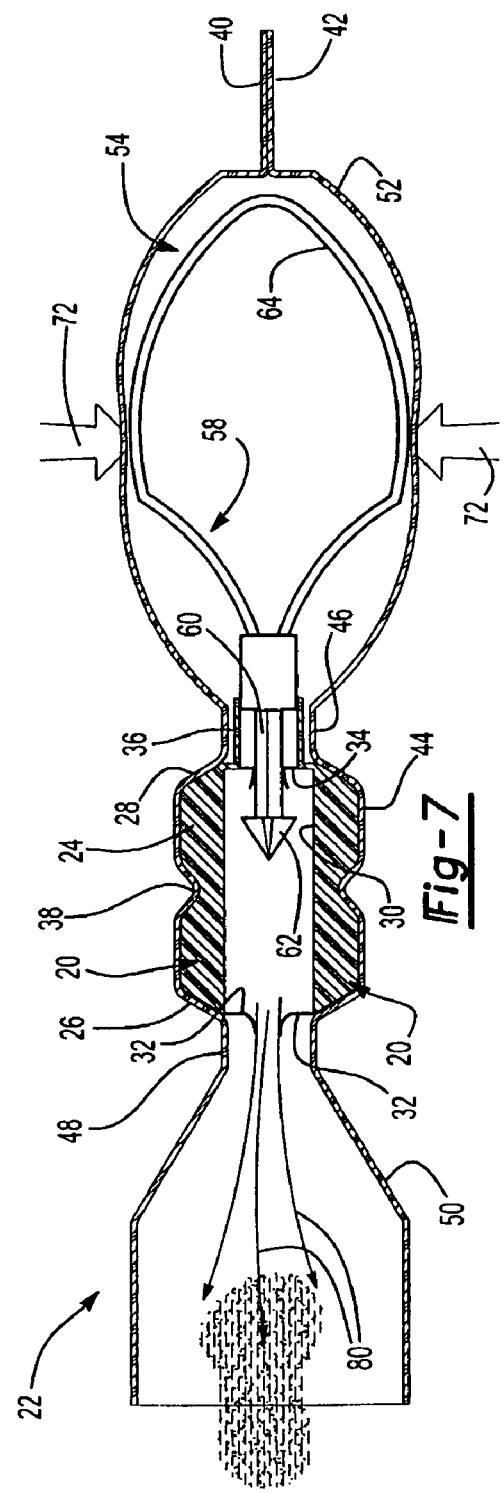

MEDICAMENT RESPIRATORY DELIVERY DEVICE

RELATED APPLICATIONS

This application is a continuation application of Ser. No. 09/879,714 filed on Jun. 12, 2001, now U.S. Pat. No. 6,443,152, which is a continuation in part application of Ser. No. 09/758,776 filed on Jan. 12, 2001, now U.S. Pat. No. 6,722,364.

FIELD OF THE INVENTION

This invention relates to medicament respiratory delivery devices for pulmonary, intranasal and buccal respiratory delivery of medicaments including an encapsulated medicament cartridge having a piercing element.

BACKGROUND OF THE INVENTION

Inhalers and atomizers are now commonly used primarily to deliver various liquid medicaments via the patient's or user's nose or mouth. As used herein, "medicament" includes any powder or liquid medicament, drug or vaccine which may be administered from a respiratory delivery device through the user's nose or mouth, sometimes referred to herein as a medicament respiratory delivery device. More recently, the prior art has proposed unit dose disposable powder medicament delivery devices, such as disclosed in U.S. Pat. No. 5,215,221, wherein a predetermined quantity or unit dose of a powder medicament is sealed in a reservoir formed between opposed thermoplastic sheets and expressed or delivered by application of manual force to a thermoformed blister which, upon actuation, breaks a burstable seal between the sheets at the entrance to the reservoir and fluidizes the powder medicament in the reservoir through a delivery tube. The delivery tube is cut prior to use.

There are several considerations affecting the design and efficacy of medicament respiratory delivery devices. First, it is important to ensure that a predetermined quantity or dose of medicament is consistently delivered to the user with each application. Second, because respiratory therapy often requires numerous applications, the cost of providing the dosage should also be considered. That is, it is desirable that the medicament respiratory delivery device consistently express substantially all of the medicament to the user and that the delivery device is not susceptible to user error in operation. Third, it is important that the medicament be properly disbursed or entrained in the conveying fluid. Further considerations include operating complexity, cost of the device, portability and size of the delivery device.

The embodiments of the medicament respiratory delivery devices and medicament cartridge of this invention provides a reproducible, high level of clearance of medicament or emitted dose from the cartridge upon actuation with modest gas pressure.

SUMMARY OF THE INVENTION

The medicament respiratory delivery device of this invention includes a housing having a chamber, an inlet communicating with the chamber, and an outlet preferably generally coaxially aligned with the inlet and a medicament cartridge located within the chamber. The medicament cartridge includes a body portion having opposed ends and a passage extending through the body portion through the opposed ends. In the most preferred embodiment, the passage is generally cylindrical, but may have other shapes including an hourglass shape. The passage includes the medicament, which may be a unit dose of a liquid or powder medicament, drug or vaccine as discussed further hereinbelow. One end of the passage is sealed with a pierceable closure which may be formed during molding of the cartridge and the opposed end of the cartridge passage opposite the outlet of the medicament delivery device is sealed with a burstable membrane, preferably comprising a thin sheet of polyolefin or a polyolefin blend or copolymer having a thickness between 0.3 and 1.5 mils and a burst pressure of between 1.2 and 10 atmospheres, more preferably less than 5 atmospheres and most preferably between 1.5 and 4 atmospheres. The term polyolefin is understood to mean a polymer containing olefin units such as, for example, ethylene, propylene or 1-butene units or any other alpha-olefin. Polyolefin as used herein includes polyethylene, polypropylene, ethylene-.alpha. olefin copolymer, wherein the alpha olefin having from 3 to 20, preferably 4 to 8 carbon atoms, polyolefin copolymers made by polymerizing olefins in the presence of a metallocene catalyst, ethylene-vinyl acetate copolymer, ethylene-ethyl acrylate copolymer, and ethylene-methyl acrylate copolymer. In particular, it is desirable to use polyethylene, such as low-density, linear-low-density, very-low-density, medium-density, or high-density polyethylene, or polypropylene, such as a polypropylene homopolymer, ethylene-propylene copolymer, or ethylene-propylene block copolymer. In the most preferred embodiment, the end of the cartridge at the outlet of the delivery device is convex or frustoconical surrounding the passage and a polymeric film is stretched taut over the convex surface and bonded or fused to the convex surface, thereby avoiding wrinkles or bulges in the burstable membrane which may adversely affect the consistency of the emitted dose of the delivery device.

The medicament respiratory delivery device of this invention further includes a piercing element movable to pierce the pierceable closure of the cartridge and a manually compressible pressure actuator which delivers fluid under pressure through the housing inlet upon piercing of the pierceable closure, thereby rupturing the burstable membrane and expressing the medicament in the passage entrained in fluid to the outlet of the delivery device. In the most preferred embodiment, the piercing element pierces the pierceable closure prior to delivery of sufficient pressure to the burstable membrane to rupture the membrane. In the preferred embodiment, the piercing element includes an actuator portion and a shaft portion having a piercing end and the cartridge includes an integral tubular portion coaxially aligned with the pierceable closure which receives the piercing end of the shaft and which guides the piercing end of the piercing element. In this embodiment, the actuator portion of the piercing element is located within the pressure actuator, such that actuation of the pressure actuator also moves the shaft portion of the piercing element to pierce the pierceable closure.

In the preferred embodiment of the medicament respiratory delivery device of this invention, the housing is comprised of two opposed thermoformed thermoplastic sheets bonded together, wherein the sheets have formed therebetween a central chamber, an inlet communicating with the chamber, a collapsible or compressible pressure actuator having an outlet communicating with the inlet to the chamber and an inlet opposite the inlet to the chamber preferably including a generally conical diffuser portion. The medicament cartridge is thereby encapsulated between the thermoformed thermoplastic bonded sheets forming the housing chamber. In the disclosed embodiment, the pressure actuator is bulb-shaped, preferably symmetrical with respect to the axis of the inlet and outlet of the chamber; however, the pressure actuator may also be a bellows-type pressure actuator either symmetrical with respect to the axis of the chamber inlet and outlet or extending from either of the thermoformed sheets. Where the pressure actuator is bulb-shaped or spherical, the acuator portion of the piercing element is bow-shaped having a concave arcuate portion generally conforming to the bulb-shape of the pressure actuator and a concave arcuate portion connected to or integral with the ends of the concave arcuate portion and the shaft portion is connected to the end of the concave portion, such that compression collapsing of the bulb-shaped pressure actuator collapses the actuator portion of the piercing element, driving the piercing end of the shaft through the pierceable closure of the capsule and deliver fluid under pressure to the cartridge passage, rupturing the burstable membrane and expressing entrained medicament through the outlet of the delivery device.

As set forth above, the medicament respiratory delivery device of this invention may be utilized to aerosolize any medicament, drug or vaccine, referred to herein generically as a medicament, including liquid, powder or even gaseous medicaments. For example, the cartridge may contain a unit dose of a liquid or powder medicament or the bulb may be filled with a liquid, such as a diluent or medicament, and the cartridge may be filled with a powder medicament, wherein the powder medicament is simultaneously reconstituted by a diluent, for example, and expressed by the medicament respiratory delivery device of this invention to the respiratory system of a user or patient.

The preferred embodiments of the medicament respiratory delivery device of this invention are particularly, but not exclusively, adapted for pulmonary, intranasal or buccal medicament delivery of a liquid or powder medicament, wherein the patient's inspiratory flowrate is not the driving force behind the delivery of the medicament. In the most preferred embodiment, the burstable membrane is formed of a preferentially oriented polyolefin film, preferably a uniaxially oriented polyethylene film having a thickness of about 1 mil and having a burst pressure of less than 5 atmospheres. Polyolefin films can be oriented by drawing in one or both mutually perpendicular directions in the plane of the film to impart strength thereto using methods known in the art. Oriented polyolefin films include machine direction and transverse direction orientation. Oriented polyolefin films include uniaxially or biaxially oriented films, with uniaxially oriented films being preferred. Uniaxially-oriented films have properties to their advantage for use as the burstable membrane, including relatively high stiffness, as indicated by the tensile modulus in a particular direction, usually the machine direction, compared to the transverse direction. Properties of the oriented polyolefin film can be dependent to a certain degree on the particular process conditions under which the polyolefin film was manufactured. For example, a stiffer film with lower transverse burst pressure properties would result from an orientation process incorporating a larger machine direction orientation draw ratio. Thus, oriented polyolefins films can be tailored to provide an appropriate burst pressure property within a preferred film thickness range. However, the burstable film may also be formed from various polymers, including cast polyethylene and polyethylene copolymers and scored or embossed polypropylene, acetate or polycarbonate. The medicament respiratory delivery of this device consistently delivers a predetermined quantity or dose of medicament to the respiratory system, is relatively simple and inexpensive to manufacture, and preferably is disposable following use. Other advantages and meritorious features of the medicament respiratory delivery device of this invention will be more fully understood from the following description of the preferred embodiments, the claims and the appended drawings, a brief description of which follows.

BRIEF DESCRIPTION OF THE DRAWINGS

FIG. 3 is a side cross-sectional view of FIG. 2 in the direction of view arrows 3-3;

FIG. 4 is a side cross-sectional view of the medicament respiratory delivery device as shown in FIG. 3 during actuation of the device;

FIG. 6 is a side cross-sectional view of FIG. 2 wherein the cartridge includes a powder medicament and the bulb includes a liquid diluent; and FIG. 7 illustrates the medicament respiratory delivery device of FIG. 4 during actuation of the pressure actuator.

DETAILED DESCRIPTION OF A PREFERRED EMBODIMENT

Figure 1:
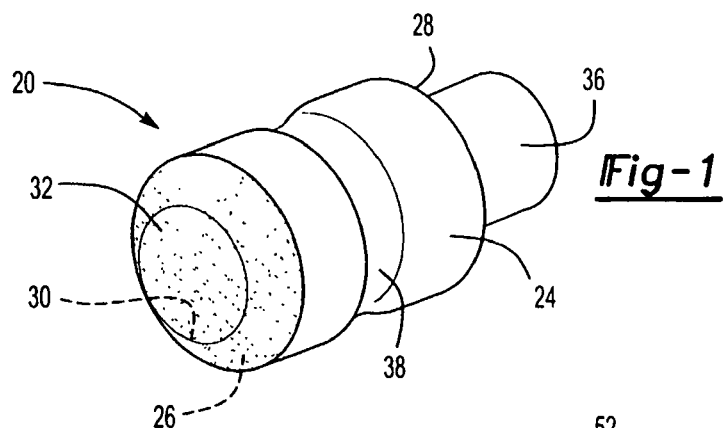
FIG. 1 is a perspective view of a medicament cartridge for the medicament respiratory delivery device of this invention.
Figure 2:
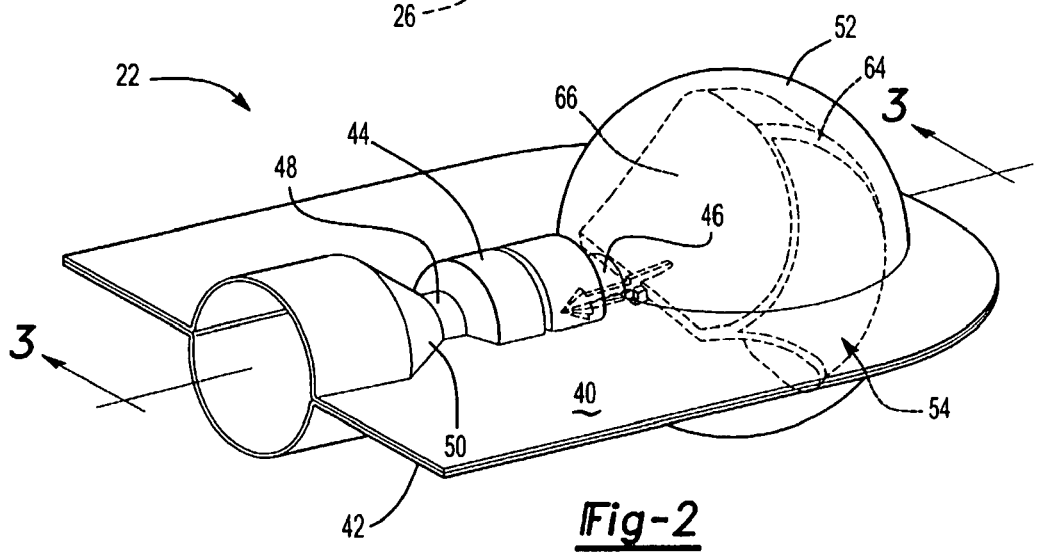
FIG. 2 is a top perspective view of a preferred embodiment of the medicament respiratory delivery device of this invention.

FIG. 1 illustrates a preferred embodiment of the medicament cartridge 20 for the embodiment of the medicament respiratory delivery device 22 illustrated in FIG. 2. The cartridge 20 includes a body 24 having opposed ends 26 and 28 and a passage 30 extending through the opposed ends. In this embodiment, one end 26 serves as the outlet end and the opposed end 28 serves as the inlet end as described further below. The outlet end 26 includes a burstable membrane 32 as described above and the inlet end 28 includes a pierceable closure 34 as shown in FIGS. 3 and 4. In the preferred embodiment, the inlet end 28 further includes a tubular guide 36 for the piercing element as described herein below. The body portion further includes a generally V-shaped groove 38 for ease of handling.

In the preferred embodiment of the medicament cartridge 20, the outlet end 26 of the body 24 is convex or frusto-conical surrounding the passage 30 and the burstable membrane 32 comprises a thin polyolefin film which is stretched taut over the convex end 26 and bonded to the convex end, thereby avoiding wrinkles in the burstable membrane 32 which may adversely affect the consistency of the emitted dose from the medicament respiratory delivery device, particularly at lower pressures. In the preferred embodiment, the burstable membrane 32 is formed from a thin sheet or film of polyolefin or a polyolefin copolymer, most preferably polyethylene or a polyethylene copolymer having a thickness of between 0.3 and 1.5 mils and a burst pressure of between 1.2 and 10 atmospheres, more preferable less than 5 atmospheres and most preferably between 1.5 and 4 atmospheres. The film is heat bonded or fused to the convex surface 26 of the outlet end of the body 24. In the most preferred embodiment, the burstable membrane is formed from a thin preferentially or uniaxially oriented polyethylene film as discussed further below.

The opposed end of the passage 30 is sealed with a pierceable closure 34 as shown in FIGS. 3 and 4 and a tubular guide 36 is perpendicular to the pierceable closure 34 and coaxial with the passage 30. The pierceable closure 34 may be formed of any suitable material which may be pierced during actuation of the medicament respiratory delivery device. In a most preferred embodiment, the body 24 of the cartridge is formed of the same or a chemically similar polymer as the burstable membrane 32 and the tubular guide 36 and pierceable closure 34 is formed during injection molding of the cartridge body 24. Thus, the body 24, pierceable closure 34 and tubular extension 36 may, for example, be formed of polyolefin polyethylene or a polyolefin copolymer including polyethylene. Included are metallized films of polyolefins.

The embodiment of the medicament respiratory delivery device shown in FIG. 2 and the following figures may be formed from opposed thermoformed thermoplastic sheets 40 and 42 bonded together by conventional vacuum forming techniques. However, it will be understood that the components of the medicament respiratory delivery device of this invention may comprise separate elements or components utilizing the advantages of the medicament cartridge 20 described hereinbelow. In the disclosed embodiment, the housing formed by the thermoformed thermoplastic sheets 40 and 42 includes an intermediate chamber 44 which encapsulates the cartridge 20, the housing having an inlet 46 and an outlet 48 which are preferably coaxially aligned with the passage 30 through the cartridge and thus also coaxially aligned with the burstable membrane 32 and pierceable closure 34 as best shown in FIGS. 3 and 4. In the disclosed embodiment, the outlet 48 includes a generally conical diffuser portion 50 integrally formed between the sheets 40 and 42. However, as will be understood by those skilled in this art, the configuration of the outlet will depend upon the application of the medicament respiratory delivery device of this invention.

The disclosed embodiment of the medicament respiratory delivery device 22 of this invention further includes a manually compressible pressure actuator 52 and a piercing element 54. In the preferred embodiment of the medicament respiratory delivery device of this invention, the pressure actuator 52 and the piercing element 54 cooperate to first pierce the pierceable closure 34 of the medicament cartridge and then deliver fluid under pressure through the pierced opening, as shown in FIG. 4, to burst the burstable membrane 32 and express the medicament in the passage 30 through the outlet 48 as described hereinbelow. In the disclosed embodiment, the pressure actuator 52 is bulb-shaped and integrally formed between the sheets 40 and 42 as best shown in FIGS. 2 and 3. In the most preferred embodiment, the bulb-shaped pressure actuator 52 is generally spherical and concentric with the axis 56 of the cylindrical passage 30 through the cartridge. However, as set forth above, the pressure actuator may be a separate collapsible bulb or bellows-type actuator (not shown) or the pressure actuator may extend from either of the sheets 40 or 42. A concentric bulb or spherical actuator is preferred for ease of operation and for use with the piercing element 54 now described.

Figure 5:
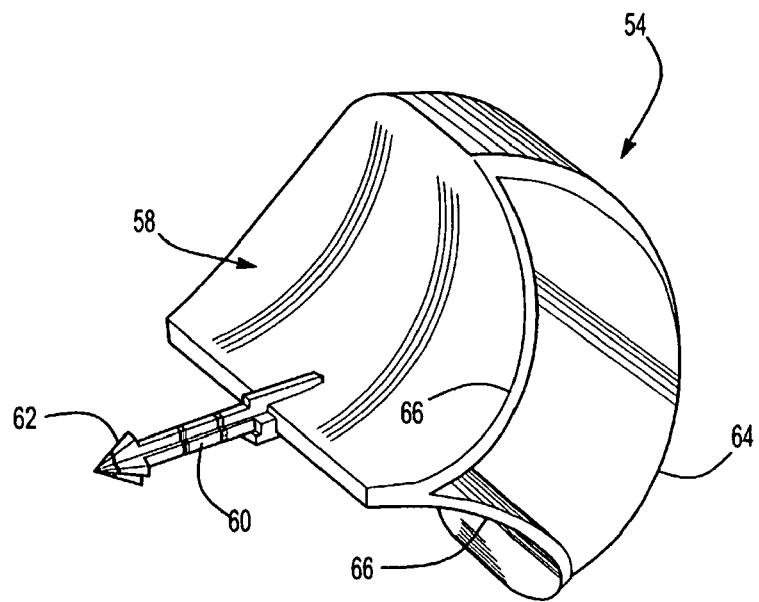
FIG. 5 is a perspective view of the piercing element shown in FIG. 2.

The disclosed embodiment of the piercing element 54 includes a bow-shaped actuator portion 58 and a shaft portion 60 having an enlarged sharp piercing end 62. As best shown in FIGS. 3 to 5, the bow-shaped actuator portion 58 includes a convex portion 64, which generally conforms to the inside shape of the spherical bulb 52, and concave portions 66 integral with the ends of the convex portions 64 forming a bow-shape and the shaft 60 is attached to the end of the concave portions 58, as best shown in FIG. 5. The piercing element 54 may be formed from a suitable resilient flexible polymer such as polyethylene, polypropylene, etc. by injection molding.

As set forth above, the housing of the medicament respiratory delivery device 22 may be vacuum formed from various thermoplastic polymers, including polyethylene, polypropylene, acetate, polycarbonate, etc. As will be understood, the sheets 40 and 42 may be separately vacuum formed, the cartridge 20 and the piercing element 54 is then assembled into one of the vacuum formed sheet halves and the vacuum formed sheets may then be heat fused together around the periphery as shown. As set forth above, the cartridge 20 may be filled with any suitable medicament, such as the liquid medicament 70 shown in FIG. 3. The cartridge may be filled with medicament by injection molding the body 24 and the pierceable closure 34 and integral guide tube 36. The medicament is then inserted into the cartridge through the open exit end 26 through the passage 30. Finally, the burstable membrane 32 is affixed over the frustoconical end 26 of the cartridge by stretching the film and heat bonding or fusing the film to the end 26 of the cartridge. Alternatively, the burstable membrane may be adhesively bonded to the end 26 of the cartridge.

Having described one preferred embodiment of the medicament respiratory delivery device 22 and the method of making same, the operation of the medicament respiratory delivery device will now be described with reference to FIGS. 3 and 4. As shown in FIG. 3, the passage 30 in the cartridge 20 includes a liquid medicament 70. The piercing end 62 of the shaft 60 is received in the tubular guide portion 36 of the cartridge adjacent to the pierceable closure 34. To actuate the device, the user compresses the pressure actuator 52 as shown by arrows 72 in FIG. 4. As the pressure actuator 52 is compressed, it engages the convex portion 64 of the actuator portion 58 of the piercing member as shown in FIG. 4, driving the shaft portion 60 to the left in FIG. 4, thereby driving the piercing portion 62 through the pierceable closure 34, delivering air under pressure through the tubular portion into the passage 30 of the cartridge 20, substantially simultaneously rupturing the burstable membrane 32 with a relatively modest pressure and thereby expressing the liquid medicament 70 through the bursted membrane into the diffusor 50 as shown by arrows 74 where it is received by the respiratory system of the patient or user.

FIGS. 6 and 7 illustrate an alternative use of the medicament respiratory delivery device 22, wherein the cartridge 20 is filled with a powder medicament 76 and the actuator portion 52 of the housing includes a liquid 78, such as a diluent or a second medicament. It is common practice to store dry or lypholized medicaments in powder form in a sealed vial to increase the shelf life of the medicament and reduce storage space. Such dry medicaments are conventionally reconstituted by adding a liquid, such as a diluent, which is injected into the vial through a syringe. The cartridge 20 of this invention is sealed against moisture and thus will maintain a powder medicament for an extended period of time. The medicament respiratory delivery device of this invention may thus be used to simultaneously reconstitute and express a powder medicament by storing liquid in the bulb or blister 52, which is also sealed between the sheets 40 and 42.

The operation of the medicament delivery device 22 shown in FIGS. 6 and 7 is essentially identical to the operation of the device as described above in regard to FIGS. 3 and 4. That is, the user compresses the bulb-shaped actuator 52 as shown by arrows 72, which compresses the convex portion 64 of the piercing element 54, which drives the piercing end 62 of the shaft portion 60 through the pierceable closure 34 and simultaneously delivers the liquid 78 and gas into the passage 30 of the cartridge and ruptures the burstable membrane 32. Where the liquid 78 IS a diluent, the diluent simultaneously reconstitutes the powder medicament 76 and the reconstituted liquid medicament is then expressed into the diffuser portion 50 of the medicament delivery device as shown arrows 80 to the respiratory system of the user.

As will now be understood, the medicament respiratory delivery device of this invention may be utilized to delivery various substances to the respiratory system of the user including medicaments, drugs and vaccines via the nasal, pulmonary or buccal routes used in the prevention, diagnosis, alleviation, treatment or cure of diseases. These substances may include, for example, (i) drugs such as Anti-Angiogenesis agents, Antisense, anto-ulcer, butorphanol, Calcitonin and analogs, COX-II inhibitors, desmopressin and analogs, dihydroergotamie, Dopamine agonists and antagonists, Enkephalins and other opioid peptides, Growth hormone and analogs (including growth hormone releasing hormone), Growth hormone antagonists, IgE suppressors, Insulin, insulinotropin and analogs, Ketamine, Kytril, Leutenizing hormone releasing hormone and analogs, lidocaine, metoclopramide, Midazolam, Narcotic analgesics, neuraminidase inhibitors, nicotine, Non-steroid anto-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin, (ii) Vaccines with or without carriers/adjuvants such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with arthritis, cholera, cocaine addiction, HIB, meningococcus, measles, mumps, rubella, varicella, yellow fever, Respiratory syncytial virus, pneumococcus, streptococcus. Typhoid, influenza, hepatitis, including hepatitis A, B, C and E, polio, HIV, parainfluenza, rotavirus, CMV, chlamydia, non-typeable haemophilus, moraxella catarrhalis, human papilloma virus, tuberculosis including BCG, gonorrhea, asthma, atheroschlerosis, malaria, otitis media, E-coli, Alzheimers, H. Pylori, salmonella, diabetes, cancer and herpes simplex, and (iii) other substances in all of the major therapeutics such as Agents for the common cold, Anti-addiction, anti-infectives, analgesics, anesthetics, anorexics, antiarthritics, anti-allergy agents, antiasthmatic agents, anticonvulsants, antidepressants, antidiabetic agents, anti-depressants, anti-diuretics, anti-emetics, antihistamines, anti-inflammatory agents, antimigraine preparations, antimotion sickness preparations, antineuseants, antieoplastics, anti-obesity, antiosteoporeteic, antiparkinsonism drugs, antipruritics, antipsychotics, antipyretics, anticholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofucnction, tranquilizers and vitamins including B12.

Computer modeling and testing of a prototype cartridge having a cylindrical bore or passage filled with a powder and various thin rupturable membranes indicated that a preferentially or uniaxially oriented polyethylene film having a thickness of about 0.5 mils resulted in an emitted dose of about 97% of powder from the passage with a burst pressure of about 3 atmospheres. Burst tests of burstable membranes were conducted by the applicant using a syringe to deliver gas under pressure to a cartridge having burstable membranes sealing both ends of the passage. The cartridge was placed in a test fixture simulating a medicament respiratory delivery device. The membranes of the cartridge each had a surface area of 0.049 in$^2$ (3 mm diameter). The stopper was moved through the barrel under controlled conditions at 25 in/min and the burst pressure (force divided by area) and emitted dose (i.e. percentage of powder emitted from the passage, HPLC assay) was measured. Computer modeling indicated that the most preferred embodiment of the cartridge included a burstable membrane only at the outlet or exit end of the cartridge. Thus, the medicament delivery device of this invention results in the greatest emitted dose from the passage 30 because the inlet closure 34 is ruptured by piercing prior to delivery of fluid to the passage. Prototype testing by the applicant of other burstable membranes as described above indicated that the next preferred burstable membrane film was a cast 50/50 polyolefin copolymer of ethylene and methylacrylate and having a thickness of about one mil and a burst pressure of 2 atmospheres, wherein the emitted dose was about 95%. The applicant also tested a polyethylene film having a thickness of about 0.9 mil wherein the polyethylene film had a checkerboard embossment having a burst pressure of 3 atmospheres, wherein the emitted dose was about 91%. It is also believed that the films formed from other polymers may be utilized for the burstable membrane 32 including, for example, polypropylene, acetate and polycarbonate. However, it is believed that such other films should also be scored or embossed to reduce the burst pressure of the burstable membrane. As set forth above, the pierceable closure 34 may be formed of various pierceable films or sheets. In the most preferred embodiment, the pierceable closure 34 is integrally formed with the body 24 of the cartridge, such as by injection molding. Thus, where the burstable membrane 32 is formed from a film of a polyolefin, most preferably polyethylene or polyethylene copolymer or blend and heat fused to the end 26 of the cartridge, the cartridge is most preferably formed from a polyethylene or a polyethylene copolymer, such that the pierceable membrane may also be formed of polyethylene. The thermoformed sheets 40 and 42 which form the housing may also be formed from various thermoformable plastic polymers including polyethylene, polypropylene, polycarbonates, etc.

Having described preferred embodiments of the medicament respiratory delivery device of this invention, it will be understood that various modifications may be made within the purview of the appended claims. For example, the passage 30 through the cartridge is preferably generally cylindrical; however, the passage may also include other shapes or configurations including, for example, an hourglass shape.

The invention claimed is:

1. A method for delivering a medicament to the respiratory system of a user, comprising:

providing a medicament respiratory delivery device having a chamber with a dry powder medicament contained therein and a pierceable closure sealing the chamber, a compressible pressure actuator in fluid communication with the chamber and having a liquid contained in the pressure actuator, and a piercing element having a pointed end movable relative to said chamber to pierce said pierceable closure, wherein said pressure actuator is a flexible collapsible element and at least a portion of said piercing element is located within said flexible collapsible element;
compressing the pressure actuator;
piercing the pierceable closure;
reconstituting the dry powder medicament with the liquid; and
expelling the reconstituted medicament from the medicament respiratory delivery device.

2. The method of claim 1, wherein the liquid is a diluent.

3. The method of claim 2, wherein reconstituting the dry powder medicament with the liquid and expelling the reconstituted medicament from the medicament respiratory delivery device take place substantially simultaneously.

4. The method of claim 1 wherein said medicament respiratory delivery device further comprises a guiding portion located adjacent to said chamber for receiving said pointed end, wherein said guiding portion guides said pointed end of said piercing element to pierce said pierceable closure upon movement of said piercing element.

5. The method of claim 1 wherein said piercing element includes a shaft wherein said pointed end is at a first end of the shaft.

6. The method of claim 5 wherein said piercing element includes a bow-shaped portion located within said pressure actuator connected to said shaft.

7. The method of claim 6 wherein said medicament respiratory delivery device further comprises a guiding portion located adjacent to said chamber for receiving said pointed end and at least a portion of said shaft, wherein said guiding portion guides said pointed end of said piercing element to pierce said pierceable closure upon movement of said shaft.

8. The method of claim 5 further comprising:
guiding the piercing element as said pointed end moves toward said piercable closure.

9. The method of claim 8 wherein said piercing element includes a bow-shaped portion located within said pressure actuator connected to said shaft.

10. The method of claim 9 further comprising:
compressing the bow shaped portion of said piercing element, thereby moving said pointed end toward said piercable closure.

11. The method of claim 9 wherein said bow-shaped portion of said piercing element includes a concave portion generally conforming to the shape of said pressure actuator having opposed end portions and concave portions integral with said end portions, and said shaft is connected to said convex portions.

12. The method of claim 11 further comprising:
compressing the concave portion of said piercing element, thereby moving said pointed end toward said piercable closure.

13. The method of claim wherein said medicament deliver device further comprises a cartridge, wherein a body of said cartridge is generally cylindrical and said chamber is formed between a pair of sheets, thus forming said piercable closure at either end of said body of said cartridge.

14. The method of claim 13 further comprising bursting the non-pierced sheet, thereby allowing the reconstituted medicament to be expelled from the device.

15. The method of claim 1 wherein said medicament deliver device further comprises a cartridge, wherein a body of said cartridge is generally cylindrical and said chamber is formed between a pair of sheets, thus forming said piercable closure at either end of said body of said cartridge.

16. The method of claim 15 further comprising:
inserting said cartridge into said medicament respiratory delivery device.

17. The method of claim 15 further comprising bursting the non-pierced sheet, thereby allowing the reconstituted medicament to be expelled from the device.

18. The method of claim 1 wherein said compressing step includes compressing at least a portion of said piercing element, thereby moving said pointed end toward said piercable closure.

* * * * *